US012728286B2

United States Patent
(12) United States Patent
Deasy et al.

(10) Patent No.: US 12,728,286 B2
(45) Date of Patent: Sep. 8, 2026

(54) METHODS AND SYSTEMS FOR AUTOMATED VOLUMETRIC MODULATED ARC THERAPY (VMAT) FOR EXTERNAL RADIATION THERAPY

(71) Applicant: MEMORIAL SLOAN KETTERING CANCER CENTER, New York, NY (US)

(72) Inventors: Joseph O. Deasy, New York, NY (US); Pinar Dursun Gunduz, New York, NY (US); Masoud Zarepisheh, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 414 days.

(21) Appl. No.: 18/035,370

(22) PCT Filed: Nov. 4, 2021

(86) PCT No.: PCT/US2021/058066
§ 371 (c)(1),
(2) Date: May 4, 2023

(87) PCT Pub. No.: WO2022/098875
PCT Pub. Date: May 12, 2022

(65) Prior Publication Data

US 2023/0414966 A1 Dec. 28, 2023

Related U.S. Application Data

(60) Provisional application No. 63/110,164, filed on Nov. 5, 2020.

(51) Int. Cl.
*A61N 5/10* (2006.01)
*G16H 20/40* (2018.01)

(52) U.S. Cl.
CPC ......... *A61N 5/1036* (2013.01); *A61N 5/1031* (2013.01); *A61N 5/1047* (2013.01); *G16H 20/40* (2018.01)

(58) Field of Classification Search
None
See application file for complete search history.

(56) References Cited

U.S. PATENT DOCUMENTS

2004/0001569 A1 1/2004 Luo
2005/0201516 A1 9/2005 Ruchala et al.
(Continued)

FOREIGN PATENT DOCUMENTS

WO WO-2017/167794 A1 10/2017

OTHER PUBLICATIONS

Breedveld et al: The equivalence of multi-criteria methods for radiotherapy plan optimization; Equivalence of multi-criteria methods11 , Physics in Medicine and Biology, Institute of Physics Publishing, Bristol GB, vol. 54, No. 23, Dec. 7, 2009 (Dec. 7, 2009), pp. 7199-7209.

(Continued)

*Primary Examiner* — Eliza W Osenbaugh-Stewart
(74) *Attorney, Agent, or Firm* — Foley & Lardner LLP

(57) ABSTRACT

Systems and methods for volumetric modulated arc therapy (VMAT) treatment planning include a processor determining, using a current solution of a non-convex VMAT optimization problem, a search region defining a corresponding spatial movement range for each leaf of a plurality of leaves of a MLC. The current solution can include first positions of the plurality of leaves of the MLC. The processor can merge, for each spatial movement range of a corresponding leaf, beamlets associated with the spatial movement range, and transform the nonconvex VMAT optimization problem into a convex VMAT optimization based on the merging of b (Continued)

camlets associated with each spatial movement range. The processor can solve the convex VMAT optimization problem to determine at least second positions of the plurality of leaves of the MLC.

20 Claims, 10 Drawing Sheets

(56) References Cited

U.S. PATENT DOCUMENTS

| | | | | |
|---|---|---|---|---|
| 2007/0041495 | A1 | 2/2007 | Olivera et al. | |
| 2007/0041497 | A1 | 2/2007 | Schnarr et al. | |
| 2008/0298550 | A1 | 12/2008 | Otto | |
| 2011/0081002 | A1 | 4/2011 | Keall et al. | |
| 2011/0107270 | A1 | 5/2011 | Wang et al. | |
| 2011/0255665 | A1 | 10/2011 | Breedveld | |
| 2012/0203053 | A1 | 8/2012 | Kilby et al. | |
| 2013/0072742 | A1 | 3/2013 | Nord et al. | |
| 2017/0014642 | A1 | 1/2017 | An et al. | |
| 2017/0036043 | A1 | 2/2017 | Dilmanian et al. | |
| 2017/0177812 | A1 | 6/2017 | Sjolund | |
| 2018/0280725 | A1 | 10/2018 | Sheng | |
| 2019/0030370 | A1 | 1/2019 | Hibbard | |
| 2019/0030372 | A1 | 1/2019 | Macdonald et al. | |
| 2019/0255354 | A1 | 8/2019 | Nordstrom et al. | |
| 2021/0020296 | A1* | 1/2021 | Sjölund ................ | A61N 5/1031 |
| 2022/0168592 | A1* | 6/2022 | Neukirchen ......... | A61N 5/1036 |

OTHER PUBLICATIONS

Craft et al: "An Approach for Practical Multiobjective IMRT Treatment Planning", International Journal of Radiation: Oncology Biology Physics, vol. 69, No. 5, Oct. 24, 2007 (Oct. 24, 2007), pp. 1600-1607.

Fu et al. "A Convex Optimization Approach to Radiation Treatment Planning with Dose Constraints." In: Cornell University Library/ Physics/ Medical Physics, Nov. 24, 2018.

International Preliminary Report on Patentability on PCT/US2019/ 021206 dated Sep. 17, 2020 (9 pages).

International Search Report on PCT PCT/US2019/021206 dated Jul. 23, 2019 (4 pages).

International Search Report on PCT PCT/US2021/058066 dtd Feb. 4, 2022.

Nguyen et al: "A feasibility study for predicting optimal radiation therapy dose distributions of prostate cancer patients from patient anatomy using deep learning", arxiv.org, Cornell University Library, 201 Olin Library Cornell University Ithaca, NY 14853, Sep. 26, 2017 (Sep. 26, 2017), XP081037675.

Qihui Lyu et al: "Single-arc VMAT optimization for dual-layer MLC", Physics in Medicine and Biology, Institute of Physics Publishing, Bristol GB, vol. 64, No. 9, May 2, 2019 (May 2, 2019), p. 95028, XP020336059, ISSN: 0031-9155, DOI: 10.1088/1361-6560/ABODDD [retrieved on May 2, 2019] * section 2.3, section 4 *.

* cited by examiner

METHODS AND SYSTEMS FOR AUTOMATED VOLUMETRIC MODULATED ARC THERAPY (VMAT) FOR EXTERNAL RADIATION THERAPY

CROSS REFERENCE TO RELATED APPLICATIONS

This application is a U.S. National Phase Application of International Application Number PCT/US2021/058066, filed Nov. 4, 2021, which claims priority to, and the benefit of, U.S. Provisional Application No. 63/110,164 filed on Nov. 5, 2020, and entitled "METHODS AND SYSTEMS FOR AUTOMATED volumetric modulated arc therapy (VMAT) for external radiation therapy," the content of each of which is incorporated herein by reference in its entirety.

FIELD OF THE DISCLOSURE

The present application relates generally to systems and methods for automatic radiotherapy treatment planning. Specifically, the present application relates to automatic automated volumetric modulated arc therapy (VMAT) for external radiation therapy.

BACKGROUND

Volumetric modulated arc therapy (VMAT) is a radiation therapy technique where a linear accelerator or a radiation machine delivers radiation to a patient continuously as its gantry rotates around the patient. Each rotation is called, or referred to as, an arc. A treatment session may involve one or more rotations or arcs. A multi-leaf collimator (MLC) can be mounted on the head of the linear accelerator (or radiation machine) to continuously shape the delivered radiation beam as the linear accelerator (or radiation machine) rotates around the patient. The MLC includes a set of metal leaves that move in-and-out and block parts of the radiation to modulate the beam and make the radiation more conformal to the shape of a planning target volume (PTV), such as a tumor.

Planning a VMAT treatment usually involves optimizing the continuous shaping of the radiation beam or arc, the radiation dose rate and/or the rotation speed of the gantry of the linear accelerator (or radiation machine) to generate highly conformal dose distributions. The goal is to deliver a desired, or preset, radiation dose to the PTV while minimizing the radiation dose to the organs surrounding the PTV or organs at risk (OARs). The continuous delivery of radiation, e.g., instead of discrete radiation beams at few angles, as the gantry rotates around the patients makes the treatment time for VMAT significantly shorter compared to, for example, treatment time for intensity modulated radiation therapy (IMRT). Also, the capability and flexibility to continuously shape the radiation beam as the gantry rotates allows for a dose distribution that conforms more accurately with the shape of the PTV.

VMAT treatment planning involves determining the parameters of the linear accelerator (or radiation machine) to achieve the goal of delivering the desired, or preset, radiation dose to the PTV while minimizing the radiation dose to the OARs. The linear accelerator parameters include the gantry rotation speed, the radiation intensity over time (or as the gantry rotates) and/or the positions of the MLC leaves over time (or as the gantry rotates). The determination of the linear accelerator (or radiation machine) parameters can be performed for various radiation treatment sessions. Also, in determining the linear accelerator (or radiation machine) parameters, the patient specific anatomy and geometry, e.g., tumor type, tumor shape, tumor location, shapes and locations of OARs and/or the physician's prescription dose, are taken into account.

SUMMARY

According to one aspect, a method of automated volumetric modulated arc therapy (VMAT) treatment planning can include one or more processors determining, using a current solution of a non-convex VMAT optimization problem, a search region defining a corresponding spatial movement range for each leaf of a plurality of leaves of a multi-leaf collimator (MLC). The current solution can include first positions of the plurality of leaves of the MLC. The one or more processors can merge, for each spatial movement range of a corresponding leaf, beamlets associated with the spatial movement range, and transform the nonconvex VMAT optimization problem into a convex VMAT optimization based on the merging of beamlets associated with each spatial movement range. The one or more processors can solve the convex VMAT optimization problem to determine at least second positions of the plurality of leaves of the MLC.

According to one other aspect, a radiation treatment planning system for performing automated volumetric modulated arc therapy (VMAT) treatment planning can include one or more processors and a memory to store computer code instructions. The computer code instructions, when executed, can cause the one or more processors to determine, using a current solution of a non-convex VMAT optimization problem, a search region defining a corresponding spatial movement range for each leaf of a plurality of leaves of a multi-leaf collimator (MLC). The current solution can include first positions of the plurality of leaves of the MLC. The one or more processors can merge, for each spatial movement range of a corresponding leaf, beamlets associated with the spatial movement range, and transform the nonconvex VMAT optimization problem into a convex VMAT optimization based on the merging of beamlets associated with each spatial movement range. The one or more processors can solve the convex VMAT optimization problem to determine at least second positions of the plurality of leaves of the MLC.

According to yet one other aspect, a computer readable medium can include computer code instructions stored thereon. The computer code instructions when executed can cause one or more processors to perform a method that includes determining, using a current solution of a non-convex VMAT optimization problem, a search region defining a corresponding spatial movement range for each leaf of a plurality of leaves of a multi-leaf collimator (MLC). The current solution can include first positions of the plurality of leaves of the MLC. The one or more processors can merge, for each spatial movement range of a corresponding leaf, beamlets associated with the spatial movement range, and transform the nonconvex VMAT optimization problem into a convex VMAT optimization based on the merging of beamlets associated with each spatial movement range. The one or more processors can solve the convex VMAT optimization problem to determine at least second positions of the plurality of leaves of the MLC.

DETAILED DESCRIPTION

For purposes of reading the description of the various embodiments below, the following descriptions of the sections of the specification and their respective contents may be helpful:

Section A describes a computing and network environment, which may be useful for practicing embodiments described herein.

Section B describes a non-convex formulation of a VMAT optimization.

Section C describes methods of automated VMAT treatment planning.

Section D discusses simulation results.

A. Computing and Network Environment

In addition to discussing specific embodiments of for automated VMAT treatment planning, it may be helpful to describe aspects of the operating environment as well as associated system components (e.g., hardware elements) in connection with the methods and systems described herein.

Figure 1A:
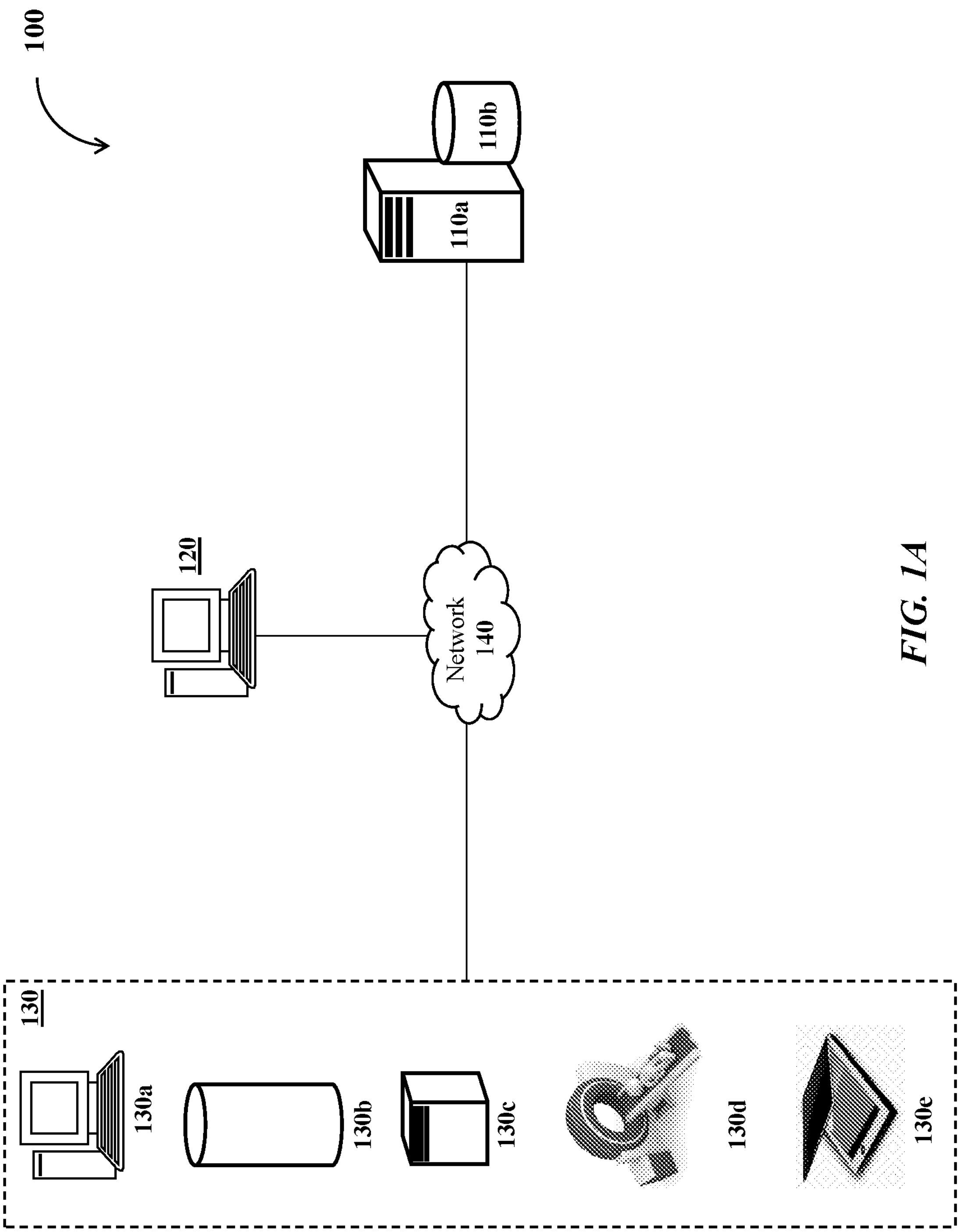
FIG. 1A shows a block diagram illustrating an example computer environment for implementing methods and processes described herein, according to example embodiments described in this disclosure.

FIG. 1A illustrates an example computer environment 100 that can be used to provide a network-based implementation of the automated VMAT treatment planning methods described herein. The computer environment 100 can include a computer server 110*a*, system database 110*b*, a user computing device 120 and electronic data sources 130*a-e* (collectively electronic data source 130). The above-mentioned components may be connected to each other through a network 140. The examples of the network 140 may include, but are not limited to, private or public LAN, WLAN, MAN, WAN, and the Internet. The network 140 may include both wired and wireless communications according to one or more standards and/or via one or more transport mediums.

The communication over the network 140 may be performed in accordance with various communication protocols such as Transmission Control Protocol and Internet Protocol (TCP/IP), User Datagram Protocol (UDP), and IEEE communication protocols. In one example, the network 140 may include wireless communications according to Bluetooth specification sets or another standard or proprietary wireless communication protocol. In another example, the network 140 may also include communications over a cellular network, including, e.g., a GSM (Global System for Mobile Communications), CDMA (Code Division Multiple Access), EDGE (Enhanced Data for Global Evolution) network.

The computer environment 100 is not necessarily confined to the components described herein and may include additional or alternative components, not shown for brevity, which are to be considered within the scope of the embodiments described herein.

In some implementations, the computer server 110*a* can be configured to execute computer instructions to perform any of the methods described herein or operations thereof. The computer server 110*a* may generate and display an electronic platform to display information indicative of, or related to, a VMAT radiation treatment plan. The electronic platform may include graphical user interface (GUI) displayed on the user computing device 120. An example of the electronic platform generated and hosted by the computer server 110*a* may be a web-based application or a website configured to be displayed on different electronic devices, such as mobile devices, tablets, personal computer, and the like (e.g., user computing device 120).

The computer server 110*a* may host a website accessible to end-users, where the content presented via the various webpages may be controlled based upon each particular user's role or viewing permissions. The computer server 110*a* may be any computing device comprising a processor and non-transitory machine-readable storage capable of executing the various tasks and processes described herein. Non-limiting examples of such computing devices may include workstation computers, laptop computers, server computers, laptop computers, and the like. While the computer environment 100 includes a single computer server 110*a*, in some configurations, the computer server 110*a* may include any number of computing devices operating in a distributed computing environment.

The computer server 110*a* may execute software applications configured to display the electronic platform (e.g., host a website), which may generate and serve various webpages to each user computing device 120. Different users operating the user computing device(s) 120 may use the website to view and/or interact with the output VMAT treatment plans.

In some implementations, the computer server 110*a* may be configured to require user authentication based upon a set of user authorization credentials (e.g., username, password, biometrics, cryptographic certificate, and the like). In such implementations, the computer server 110*a* may access the system database 110*b* configured to store user credentials, which the computer server 110*a* may be configured to reference in order to determine whether a set of entered credentials (purportedly authenticating the user) match an appropriate set of credentials that identify and authenticate the user.

In some configurations, the computer server 110*a* may generate and host webpages based upon a particular user's role (e.g., administrator, employee, and/or bidder). In such implementations, the user's role may be defined by data fields and input fields in user records stored in the system database 110*b*. The computer server 110*a* may authenticate the user and may identify the user's role by executing an access directory protocol (e.g. LDAP). The computer server 110*a* may generate webpage content that is customized according to the user's role defined by the user record in the system database 110*b*.

In some embodiments, the computer server 110*a* may receive medical images, masks, indication of a prescription radiation doze and/or other subject/patient specific medical data. The computer server 110*a* may receive information indicative of characteristics, e.g., machine make and model, of a linear accelerator (or radiation machine) to be used for radiation treatment. The computer server 110*a* may receive data as input via an input device, from a data repository, from other devices or a combination thereof. The computer server 110*a* may process the data, e.g., by executing automated VMAT treatment planning methods described herein, and display an indication of an output VMAT treatment plan on the electronic platform. For instance, in a non-limiting example, a user operating the computing device 130*a* may upload a series of images of a CT scan or other medical images using the electronic platform. The computer server 110*a* can determine the VMAT treatment plan based on the input data, and display the results via the electronic platform on the user computing device 120 or the computing device 130*a*. The computer server 110*a*, the user computing device 120 and/or the computing device 130*a* may be any computing device comprising a processor and a non-transitory machine-readable storage medium capable of performing the various tasks and processes described herein. Non-limiting examples of a network node may be a workstation computer, laptop computer, tablet computer, and server computer. In operation, various users may use user computing devices 120 and or computing device 130*a* to access the GUI operationally managed by the computer server 110*a*.

The electronic data sources 130 may represent various electronic data sources that contain and/or retrieve medical images of patients/subjects, medical prescription data, medical reports and/or other patient/subject specific data. For instance, database 130*b* and third-party server 130*c* may represent data sources providing the corpus of data, e.g., medical images, masks, prescription dose, or other medical data, needed for the computer server 110*a* to determine VMAT treatment plans. The computer server 110*a* may also retrieve the data directly from a medical scanner 130*e* and/or medical imaging device 130*d* (e.g., CT scan machine).

In some implementations, the methods described herein or operations thereof can be implemented by the user device 120, any of the electronic devices 130, the computer server 110*a* or a combination thereof.

While FIG. 1A shows a network-based implementation, it is to be noted that methods described herein can be implemented by a single computing device that receives the medical images and medical data for a patient and determines a VMAT radiation treatment plan according to methods described herein.

Figure 1B:
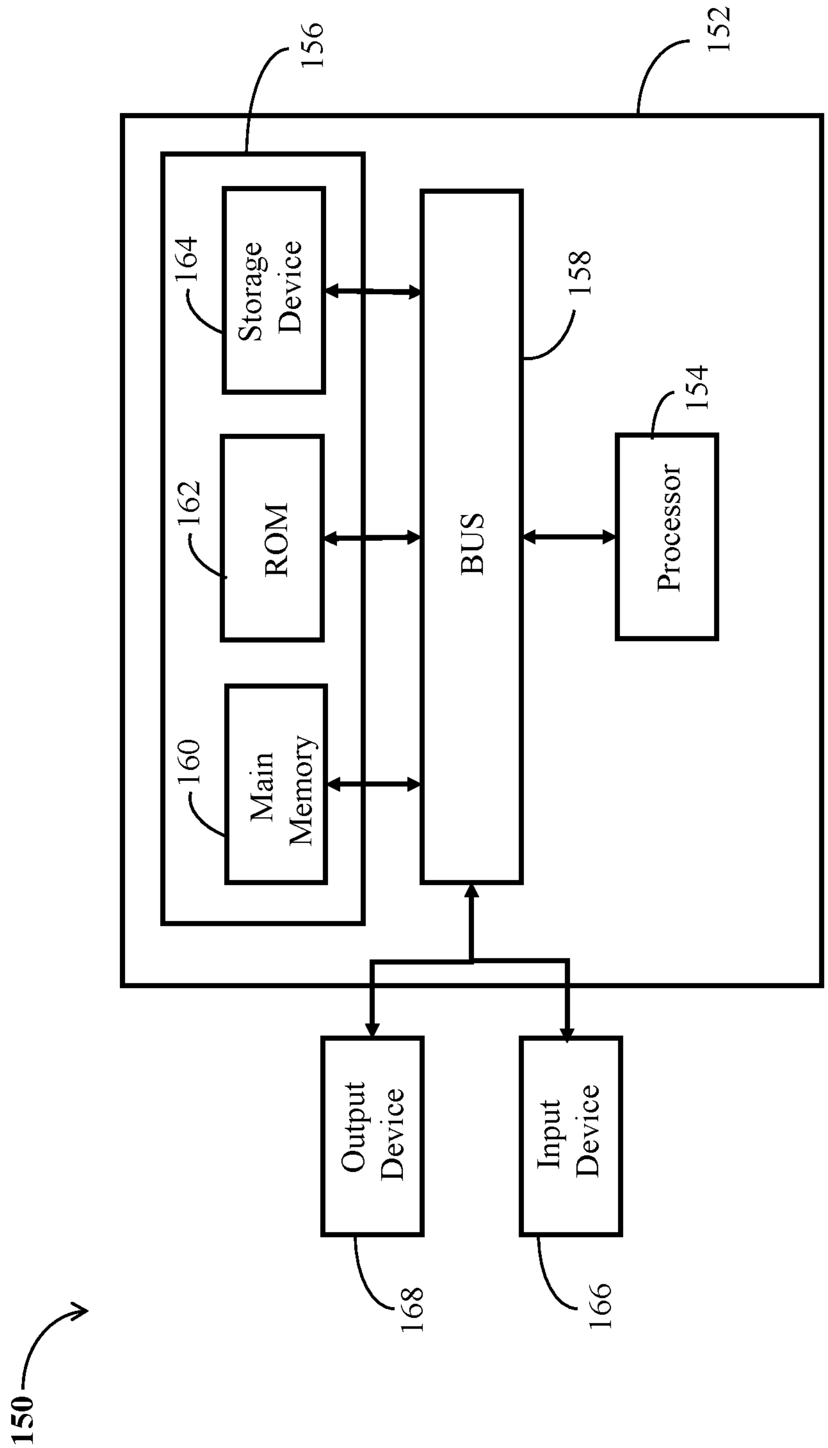
FIG. 1B is a block diagram depicting one implementation of a system architecture, according to example embodiments described in this disclosure.

Referring to FIG. 1B, a block diagram depicting one implementation of a system architecture for a computing system 150 that may be employed to implement methods described herein is shown, according to inventive concepts of the current disclosure. The computing system 150 can include a computing device 152. The computing device 152 can represent an example implementation of any of the devices 110*a*, 120 and/or 130*a-e* of FIG. 1A. For instance, the computing device 152 can include, but is not limited to, a computed tomography (CT) scanner, a medical linear accelerator device, a desktop, a laptop, a hardware computer server, a workstation, a personal digital assistant, a mobile computing device, a smart phone, a tablet, or other type of computing device. The computing device 152 can include one or more processors 154 to execute computer code instructions, a memory 156 and a bus 158 communicatively coupling the processor 154 and the memory 156.

The one or more processors 154 can include a microprocessor, a general purpose processor, a multi-core processor, a digital signal processor (DSP) or a field programmable gate array (FPGA), an application-specific integrated circuit (ASIC) or other type of processor. The one or more processors 154 can be communicatively coupled to the bus 158 for processing information. The memory 156 can include a main memory device 160, such as a random-access memory (RAM) other dynamic storage device, coupled to the bus 158 for storing information and instructions to be executed by the processor 154. The main memory device 160 can be used for storing temporary variables or other intermediate information during execution of instructions (e.g., related to methods described herein such as method 200) by the processor 154. The computing device 152 can include a read-only memory (ROM) 162 or other static storage device coupled to the bus 158 for storing static information and instructions for the processor 154. For instance, the ROM 162 can store medical images of patients, for example, received as input. The ROM 162 can store computer code instructions related to, or representing an implementation of, methods described herein. A storage device 164, such as a solid state device, magnetic disk or optical disk, can be coupled to the bus 158 for storing (or providing as input) information and/or instructions.

The computing device 152 can be communicatively coupled to, or can include, an input device 166 and/or an output device 168. The computing device 102 can be coupled via the bus 158 to the output device 168. The output device 168 can include a display device, such as a Liquid Crystal Display (LCD), Thin-Film-Transistor LCD (TFT), an Organic Light Emitting Diode (OLED) display, LED display, Electronic Paper display, Plasma Display Panel (PDP), or other display, etc., for displaying information to a user. The output device 168 can include a communication interface for communicating information to other external devices. An input device 166, such as a keyboard including alphanumeric and other keys, may be coupled to the bus 158 for communicating information and command selections to the processor 154. In another implementation, the input device 166 may be integrated within a display device, such as in a touch screen display. The input device 166 can include a cursor control, such as a mouse, a trackball, or cursor direction keys, for communicating direction information and command selections to the processor 154 and for controlling cursor movement on the display device.

According to various implementations, the methods described herein or respective operations can be implemented as an arrangement of computer code instructions that are executed by the processor(s) 154 of the computing system 150. The arrangement of computer code instructions can be read into main memory device 160 from another computer-readable medium, such as the ROM 162 or the storage device 164. Execution of the arrangement of computer code instructions stored in main memory device 160 can cause the computing system 150 to perform the methods described herein or operations thereof. In some implementations, one or more processors 154 in a multi-processor arrangement may be employed to execute the computer code instructions representing an implementation of methods or processes described herein. In some other implementations, hard-wired circuitry may be used in place of or in combination with software instructions to effect illustrative implementation of the methods described herein or operations thereof. In general, implementations are not limited to any specific combination of hardware circuitry and software. The functional operations described in this specification can be implemented in other types of digital electronic circuitry, in computer software, firmware, hardware or a combination thereof.

B. Non-Convex Formulation of VMAT Optimization

Volumetric modulated arc therapy (VMAT), initially introduced as intensity modulated arc therapy (IMAT), has been gaining popularity in the past years and became a method of choice in external radiotherapy for many disease sites. The VMAT radiation delivery period is relatively short compared to the radiation delivery period of IMIRT, making VMAT an appealing delivery technique from the resource utilization perspective. The relatively short radiation delivery period of VMAT makes VMAT treatment plans less prone to uncertainties stemming from patient movements during radiation treatment sessions. From the algorithm design perspective though, VMAT represents a much larger and more challenging optimization problem compared to IMRT. Similar to IMRT, VMAT optimization can be achieved via a two-step fluence map optimization approach or a direct aperture optimization (DAO) approach. The two-step fluence map optimization approach includes optimizing, in a first step, the fluence profiles at incident beams, and then decomposing the optimal fluence profiles into deliverable apertures over the corresponding arcs in a second step. The DAO approach involves a direct optimization of the shapes and intensities of the apertures for each beam.

In the two-step approach, the fluence map optimization in the first step is usually a convex problem. As to the second step, the decomposition of the optimal fluence profiles into deliverable apertures over the corresponding arcs can be achieved using computationally inexpensive arc sequencing algorithms. However, solutions to the two-step approach usually suffer from dose discrepancy between the decoupled first and second steps, which could degrade the treatment plan quality. Although the two-step IMRT optimization approach also suffers from dose discrepancy, this problem is much more pronounced in VMAT as the optimal fluence profile of each beam is converted into apertures, which are placed in the neighboring beams different from the original beam. The DAO approach optimizes the aperture shapes of each beam directly, and as such does not suffer dose discrepancy between the decoupled first and second steps. However, solving the DAO approach is challenging given the non-convexity of the resultant optimization problems mainly stemming from the non-convex relationship between the radiation machine's parameters, e.g., aperture shapes and intensities, and the patient's deposited dose.

The non-convexity of the resultant optimization problems associated with the DOA approach calls for the development of more advanced optimization algorithms or techniques. In the current disclosure, systems and methods for automated VMAT radiation treatment planning employ a new DAO algorithm for VMAT based on an advanced non-convex optimization technique known as sequential convex programming (SCP). The main idea of SCP is to solve a non-convex optimization problem by solving a sequence of approximate convex optimization problems. In the context of VMAT, constraining the leaf motions at each iteration leads to a convex approximation. The new DAO algorithm can be derived using a constrained optimization formulation that aims to optimize the planning target volume (PTV) coverage and homogeneity in the objective function subject to hard maximum and mean dose constraints on organ at risks (OARs) and PTV. In some implementations, the constrained optimization framework can be extended to hierarchical constrained optimization for automated VMAT planning. The systems and methods described herein can employ both local and global search strategies. Performance of the proposed algorithm is verified herein by comparing it against the ground-truth solution obtained by solving a corresponding mixed integer programming (MIP) formulation.

Let the delivery arc be discretized into evenly spaced beams with indices b=1, . . . , B, the patient's body be discretized into voxels with indices j=1, . . . , J, and each radiation beam be discretized into beamlets with indices i=1, . . . , I. The dose delivered to each voxel from each beamlet of unit intensity can be pre-calculated and stored as a matrix called the influence matrix, also known as the dose deposition matrix. The fluence matrix is denoted herein as A. The treatment planning problem can be formulated as a constrained VMAT optimization problem that is defined in terms of an objective function that maximizes PTV coverage and homogeneity, and hard constraints specifying, for example, maximum and mean dose requirements on the OARs and the PTV are respected as hard constraints. Such optimization problem is non-convex mainly due to the non-convex relationship between the parameters of the linear accelerator (or radiation machine), such as the positions of the MLC leaves and apertures' intensities, and the deposited (or delivered) radiation dose in the patient's body.

The goal of the VMAT optimization problem is to determine a set of apertures and their intensities, denoted herein as $\eta$, to deliver a desired or optimal radiation dose distribution that meets predefined characteristics. The desired radiation dose distribution is equal to a prescription dose within the PTV, and meets all the maximum and mean dose constraints. The objective function can be defined as a quadratic objective function to minimize deviation of the radiation distribution from the prescription dose within the PTV.

The aperture shapes can be characterized by the positions of the left and right leaves of the MLC, denoted by l and r, respectively. Let the variable x represent the beamlet intensities. For each beamlet, depending on whether it is open or fully or partially covered by a leaf, the intensity can be equal to the corresponding aperture intensity $\eta$, zero or an intensity value in-between, respectively. Let $\Phi(\eta, l, r)$ denote a function that the relationship between the beamlet intensities, or the variable x, on one side, and the leave positions and aperture intensities on the other side. That is, $x=\Phi(\eta, l, r)$.

Figure 2:
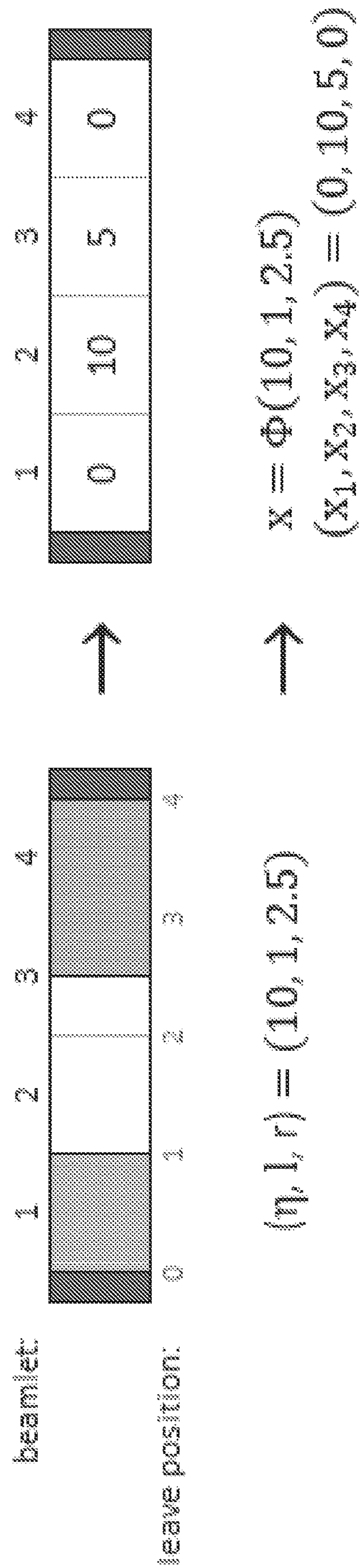
FIG. 2 is a schematic diagram illustrating a relationship or link between primary variables (η, l, r) and an auxiliary variable x, according to example embodiments of the current disclosure.

Referring to FIG. 2, a schematic diagram illustrating the link between the primary variables ($\eta$, l, r) and the auxiliary variable x is shown, according to example embodiments of the current disclosure. The cells on the left side represent various beamlets. The gray areas represent beamlets or respective portions that are covered by the MLC leaves. The cells on the right side represent entries of the vector x or the beamlet intensities. For each triplet of the primary variables ($\eta$, l, r), l, r) represents a vector of beamlet intensities at a plurality of voxels of an anatomical region of a patient or subject. While the x vector has a dimension of four entries in the example shown FIG. 3, in reality, the length of x can be much larger than four.

The VMAT optimization problem can be formulated as:

$$\min_X F(x) = \sum_{s\in\{PTV\}} \|A^s x - p\|_2^2, \qquad (1)$$

-continued $$\text{subject to: } \begin{cases} \max(A^s x) \le d_s^{max}: s \in S_{max} & (2) \\ \text{mean}(A^s x) \le d_s^{mean}: s \in S_{mean} & (3) \\ x = \Phi(\eta, l, r) & (4) \\ 0 \le l \le r \le N & (5) \\ 0 \le \eta \le U^\eta & (6) \end{cases}.$$

In equation (1), the objective function F can represent the $L^2$ norm of the mismatch between the optimized radiation dose and the prescription radiation dose within the PTV. The optimized radiation dose is denoted as $A^s x$ and the prescription radiation dose is represented by the vector p. The constraints in equations (2) and (3) represent the maximum and mean dose hard constraints of the anatomy regions or structures $S_{max}$ and $S_{mean}$, respectively. The constraint in equation (5) is meant to ensure that the left and right leaves of the MLC do not cross each other and are within their limits defined by the field size N. The constraint in equation (6) limits the aperture intensities to an intensity upper bound $U^\eta$. Equation (4) represents the relationship between the beamlet intensities and the primary variables (η, l, r), and is the main source of non-convexity and complexity of the optimization problem. Table 1 below provides a full description of the variables and notations used in the optimization problem described by equations (1)-(6).

TABLE 1

| Symbol | Description | Symbol | Description |
|---|---|---|---|
| x | Beamlet intensity or fluence map (nonnegative continuous variable) | b | Beam indice (b = 1, . . . , B) |
| p | Prescription dose | j | Voxel indices (j = 1, . . . , J) |
| η | Aperture intensity (nonnegative continuous variable) | i | Beamlet indices (i = 1, . . . , I) |
| A | Influence matrix | l, r | Positions of the left and right leaves (nonnegative continuous variables) |
| S | Structure index | $U^\eta$ | Aperture intensity upper bound |
| $A^s$ | Influence matrix for structure s | $\|\cdot\|_2^2$ | Second norm |
| $d_s^{max}$ | Max. dose limit for structure s | N | Number of columns |
| $d_s^{mean}$ | Mean dose limit for structure s | $(d)_+$ | max(d, 0) |

For a beamlet with index i belonging to beam $b_i$ and corresponding to a row $r_i$ and a column $c_i$, the function Φ can be explicitly written as:

$$\Phi(\eta_{b_i}, l_{b_i r_i}, r_{b_i r_i}) = \eta_{b_i} \times \min((\min(c_i - l_{b_i r_i}, 1))_+, (\min(r_{b_i r_i} + 1 - c_i, 1))_+, r_{b_i r_i} - l_{b_i r_i}). \quad (7)$$

The parameter $\eta_{b_i}$ represents the aperture or beam intensity. Note that the beam $b_i$ can be discretized into an array of I different beamlets, with each beamlet defined by a corresponding row and a corresponding column of the cross section area of the beam $b_i$ (or the aperture). The values $l_{b_i r_i}$ and $r_{b_i r_i}$ represent the positions of the left and right leaves along the row $r_i$. The term $c_i - l_{b_i r_i}$ represents the difference between the column index $c_i$ and the position of the left leaf along the row $r_i$. The term $(\min(c_i - l_{b_i r_i}, 1))_+$ can be indicative of whether the cell $(r_i, c_i)$ corresponding to the row $r_i$ and the column $c_i$ (or representing the corresponding to beamlet i) is fully covered, partially covered or not covered by the left leaf. For instance, a value of the term $c_i - l_{b_i r_i}$ that is smaller than or equal to zero can indicate that the cell $(r_i, c_i)$ is fully covered by the left leaf, a positive value of the term $c_i - l_{b_i r_i}$ that is smaller than 1 ca indicate that the cell $(r_i, c_i)$ is partially covered by the left leaf, and a positive value of the term $c_i - l_{b_i r_i}$ that is larger than or equal to 1 can indicate that the cell $(r_i, c_i)$ is not covered at all be the left leaf.

Similarly, the term $(\min(r_{b_i r_i} + 1 - c_i, 1))_+$ can be indicative of whether the cell corresponding to the row $r_i$ and the column $c_i$ (or the corresponding beamlet i) is fully covered, partially covered or not covered at all by the right leaf. A value of the term $r_{b_i r_i} + 1 - c_i$ that is smaller than or equal to zero can indicate that the cell $(r_i, c_i)$ is fully covered by the right leaf, a positive value of the term $r_{b_i r_i} + 1 - c_i$ that is smaller than 1 can indicate that the cell $(r_i, c_i)$ is partially covered by the right leaf, and a positive value of the term $r_{b_i r_i} + 1 - c_i$ that is larger than or equal to 1 can indicate that the cell $(r_i, c_i)$ is not covered at all be the right leaf. The term Function Φ is a complex non-convex and non-differentiable function. The term $r_{b_i r_i} - l_{b_i r_i}$ can indicate whether there is a gap between the left and right leaves or they fully cover the aperture. If $r_{b_i r_i} = l_{b_i r_i}$, then the left and right leaves, together, fully cover the aperture.

Figure 3:
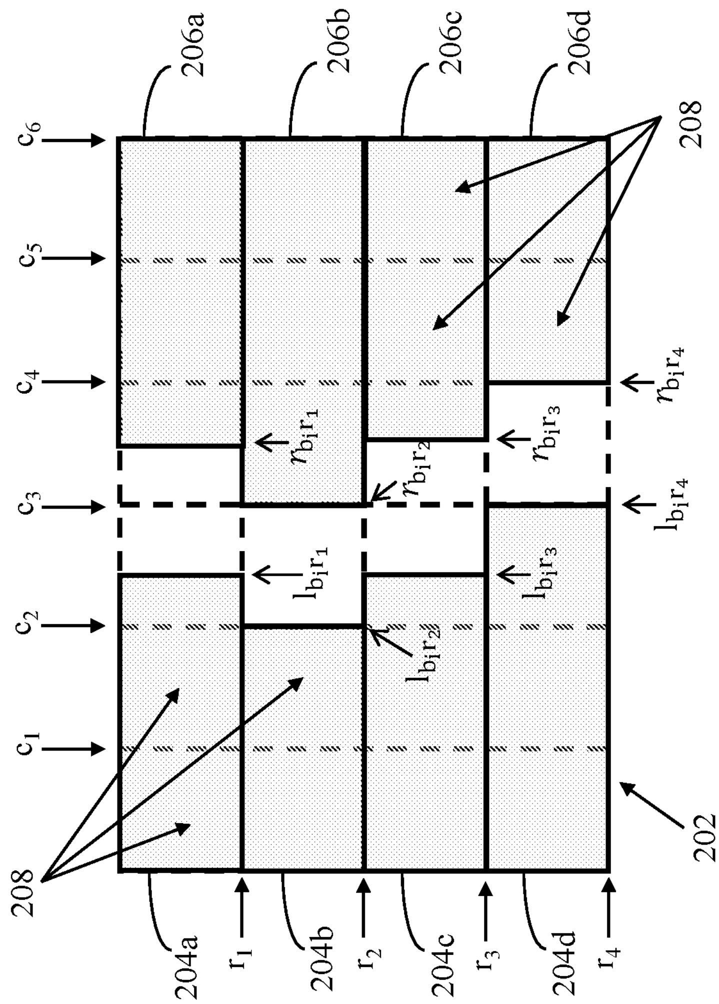
FIG. 3 shows a diagram illustrating an example arrangement of left and right leaves with respect to rows and columns of an aperture, according to some example embodiments of the current disclosure.

Referring to FIG. 3, a diagram illustrating an example arrangement of left and right leaves with respect to rows and columns of an aperture 202 is shown, according to some example embodiments of the current disclosure. The aperture 202 (or a cross section area of the radiation beam $b_1$) can be discretized into four rows and six columns. Each cell, defined by the intersection of a corresponding row and a corresponding column, represents a corresponding beamlet 208 (or a cross section area thereof). Right leaves 204*a*-204*d* and left leaves 206*a*-206*d*, shown in transparent gray, can be used to dynamically cover beamlets 208 and shape arc as the gantry rotates around the patient/subject. Positions for the left leaves 204*a*-204*d* are shown as $$l_{b_1 r_1} = \frac{c_3 + c_2}{2},\ l_{b_1 r_2} = c_2,\ l_{b_1 r_3} = \frac{c_3 + c_2}{2} \text{ and } l_{b_i r_4} = c_3$$

along a horizontal dimension of the aperture 202. Positions for the right leaves 206*a*-206*d* are shown as $$r_{b_1 r_1} = \frac{c_3 + c_4}{2},\ r_{b_1 r_2} = c_3,\ r_{b_1 r_3} = \frac{c_3 + c_4}{2} \text{ and } r_{b_i r_4} = c_4$$

along the horizontal dimension of the aperture 202.

According to the formulation in equation (7), the function Φ is a complex non-convex and non-differentiable function. These characteristics of Φ make the optimization problem described in equations (1)-(6) challenging and difficult to solve. While FIG. 3 shows four left leaves 204*a*-204*d* and four right leaves206*a*-206*d*, in general, the MLC can have any number of leaves. Also, each leaf can have another shape, e.g., not necessarily a rectangular shape, and can be positioned and arranged to move along any angle with respect to the aperture 202. Compared to equation (7), the function Φ can be formulated differently depending on, for example, the number, shapes, relative orientations and directions of motions of the leaves of the MLC. However, regardless of these factors, the function Φ may still be, in most cases if not all of them, a complex non-convex and non-differentiable function.

C. Automated VMAT Treatment Planning

Automated VMAT treatment planning methods described herein can employ a sequential convex programming (SCP) based approach. SCP is an advanced optimization method to deal with non-convex optimization problems. The main idea of SCP is to solve a non-convex optimization problem iteratively by solving a sequence of approximate convex optimization problems. The SCP-based approach can include generating, at each iteration, a convex approximation of the original non-convex problem. Such approximation is usually valid in a search space, also known and referred to herein as the trust region, around a current solution. The SCP-based approach can include determining an optimal point of the approximate convex problem, and evaluating the determined optimal point using the original non-convex problem. If the determined optimal point is better than a current solution for the original problem, the current solution can be replaced with the determined optimal point for in a next iteration. Otherwise, different optimal point can be generated or the method(s) may terminate. Determining the convex approximation can include using, or convexifying, the first or second order Taylor approximations of the non-convex constraints and/or objective function. Another convexification approach can include creating a convex approximation by leveraging the special structures and properties of the underlying problem. The approximations can be categorized into local and global approximations depending on the size of the trust region within which the original non-convex problem is represented. A local approximation is usually referred to as an approximation that represents the original problem in a small vicinity of the current solution. The local approximation strategy is usually helpful in improving the current solution locally, or in other words, converging to a local optimal solution. A global approximation, on the other hand, associates with a large trust region and aims at capturing the global shape of the original problem, and therefore, promotes convergence to a global minimum. It is very common to start with a global search, e.g., relatively large trust region, and gradually move to a local search, e.g., small trust region. The automated VMAT treatment planning method(s) described herein can include enlarging the trust region every time the optimal solution of the approximate problem is better a current solution of the original problem, e.g., to promote convergence to a global minimum, and shrink the trust region otherwise to improve the accuracy of the approximation.

Figure 4A:
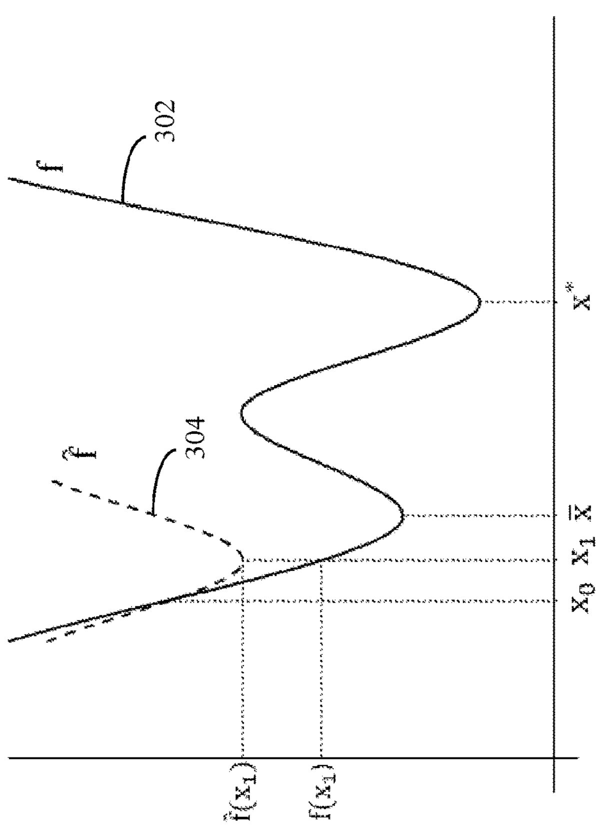
FIGS. 4A and 4B illustrate examples of local and global approximations of a one-dimensional non-convex function.
Figure 4B:
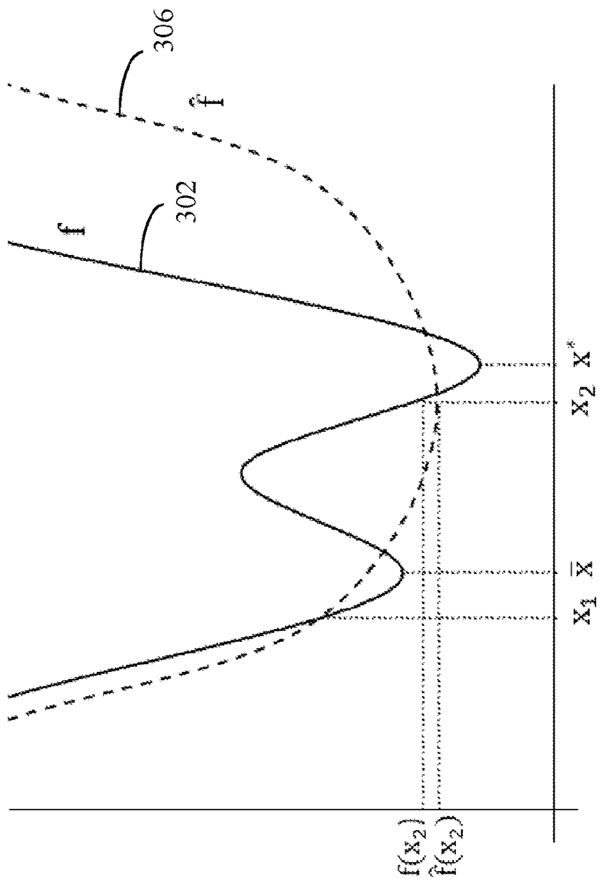

Referring to FIGS. 4A and 4B, examples of local and global approximations of a one-dimensional non-convex function are illustrated. The function $\hat{f}(.)$ 302 represents the one-dimensional non-convex function, while the functions $\hat{f}(.)$ 304 and 306 represent the local and global approximations, respectively, of the function f 302. In FIG. 4A, the local convex approximation $\hat{f}(.)$ 304 is generated around an initial point $x_0$. The local approximation $\hat{f}(.)$ 304, as illustrated in FIG. 3A provides a good approximation off 302 in the vicinity of $x_0$ since the minimum $x_1$ of $\hat{f}(.)$ 304 is closer to local the minimum $\bar{x}$ of the function $\hat{f}(.)$ 302 than the initial point $x_0$. Given the convexity of $\hat{f}(.)$, its optimal point $x_1$, which is a better solution for the original non-convex function f 302 than the initial point $x_0$, can be found and can be accepted or used as the next estimate of the solution of for the non-convex function f 302. Repeating, at each iteration, the process of generating a local approximation of the original non-convex problem based on a current solution (e.g., a solution determined at a prior iteration) can lead to a convergence to the local minimum $\bar{x}$ of the non-convex function f 302.

In FIG. 4B, the function $\hat{f}(.)$ 306 approximates the non-convex fat point $x_1$. A larger trust region, than that used to determine the local approximation 304 in FIG. 4A, is used to determine the function $\hat{f}(.)$ 306. As such, the function 306 provides a "good" approximation of the non-convex function f 302 over a range or interval that extends relatively far from the point $x_1$. As depicted in FIG. 4B, the optimal solution (or minimum)×$x_2$ of the global approximation 306 is closer to the global minimum x* of the non-convex function f(.) 302 than the starting point $x_1$. The point $x_2$ can be used in a subsequent iteration to determine a new approximation of the non-convex function f 302. The process of determining a convex approximation of the non-convex function 302 and determining a solution of the convex approximation can continue iteratively until no significant improvement can be achieved (e.g., the determined solution is close to the global minimum x* of the non-convex function f(.) 302.)

Figure 5:
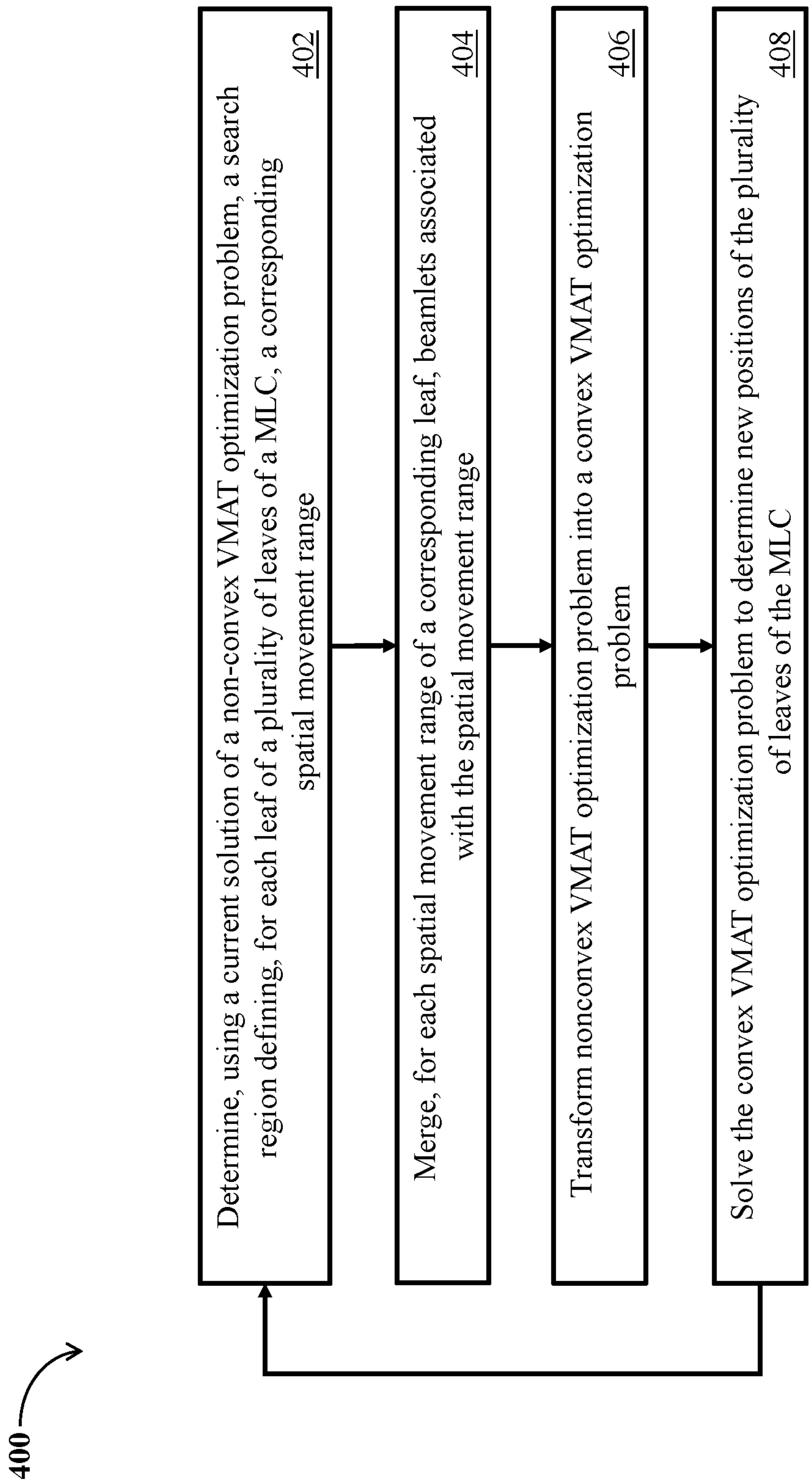
FIG. 5 shows a flowchart illustrating a method of automated volumetric arc modulated therapy (VMAT) treatment planning, according to some example embodiments of the current disclosure.

Referring to FIG. 5, a flowchart illustrating a method 400 of volumetric arc modulated therapy (VMAT) treatment planning is shown, according to some example embodiments of the current disclosure. In brief overview, the method 400 can include determining, using a current solution of a non-convex VMAT optimization problem, a search region defining or including, for each leaf of a plurality of leaves of a multi-leaf collimator (MLC), a corresponding spatial movement range (STEP 402). The method 400 can include merging, for each spatial movement range associated with a corresponding leaf of the plurality of leaves, beamlets associated with the spatial movement range (STEP 404). The method 400 can include transforming, based on the merging of the beamlets, the non-convex VMAT optimization problem into a convex VMAT optimization problem (STEP 406), and solving the convex VMAT optimization problem to determine new positions of the plurality of leaves (STEP 408). The steps 402-408 of the method 400 can be repeated iteratively until a satisfactory solution of the non-convex VMAT optimization problem is reached.

Referring to FIGS. 1A, 1B and 5, the method 400 can include the computing system 150 determining, using a current solution of a non-convex VMAT optimization problem, a search region defining or including, for each leaf of a plurality of leaves of the multi-leaf collimator (MLC), a corresponding spatial movement range (STEP 402). The computing system 150 can receive patient/subject specific data, such as medical images, masks, prescription dose and/or other medical data. The computer system 150 can determine a non-convex formulation of the VMAT optimization problem, such as the formulation described by equations (1)-(6), using the patient/subject specific data. For instance, the computing system 150 can use patient/subject specific data indicative of prescription radiation dose to construct or generate the vector p in equation (1). The computing system 150 can use medical images or masks to determine the PTV in equation (1) as well as $S_{max}$ and $S_{mean}$ in equations (2) and (3), respectively.

The method 400 can be an iterative method where the computing system 150 can repeat steps 402-408 multiple times. At a first iteration, the computing system 150 can start with determining an initial estimate of the solution of the non-convex VMAT optimization problem. At later iterations, the computing system 150 can use an estimate of the solution of the non-convex VMAT optimization problem determined at a previous iteration. The estimate of the solution can include estimates of the primary variables (η, l, r). Each of these variables can be a vector variable. For instance, the variables l and r can be vectors representing positions of multiple left and right leaves, respectively, of the MLC. The estimate of the solution of the non-convex VMAT optimization problem at each iteration is referred to herein as a current solution of the non-convex VMAT optimization problem.

Given a current solution ($\eta_k$, $l_k$, $r_k$) of the non-convex VMAT optimization problem (e.g., at the start of the $k^{th}$ iteration), the computing system 150 can determine (or define) a trust or search region that defines (or includes) a movement range for each of the leaves of the MLC. The computing system 150 can determine (or define) the search or trust region, such that each leaf of the MLC is arranged to move, from its current position, by a predefined distance forward or backward during a given iteration. For example, the search or trust region can define, for each leaf of the MLC, a movement range of one beamlet backward to one beamlet forward. The determined search or trust region can be a continuous region or a set of disconnected regions.

Figure 6B:
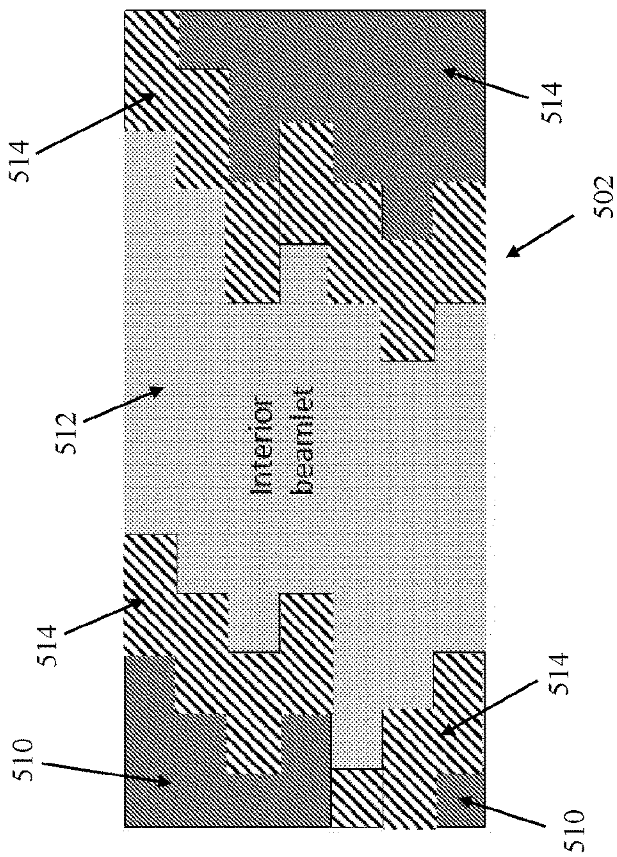
FIGS. 6A and 6B show diagrams illustrating generation of a trust or search region, according to example embodiments of the current disclosure.
Figure 6A:
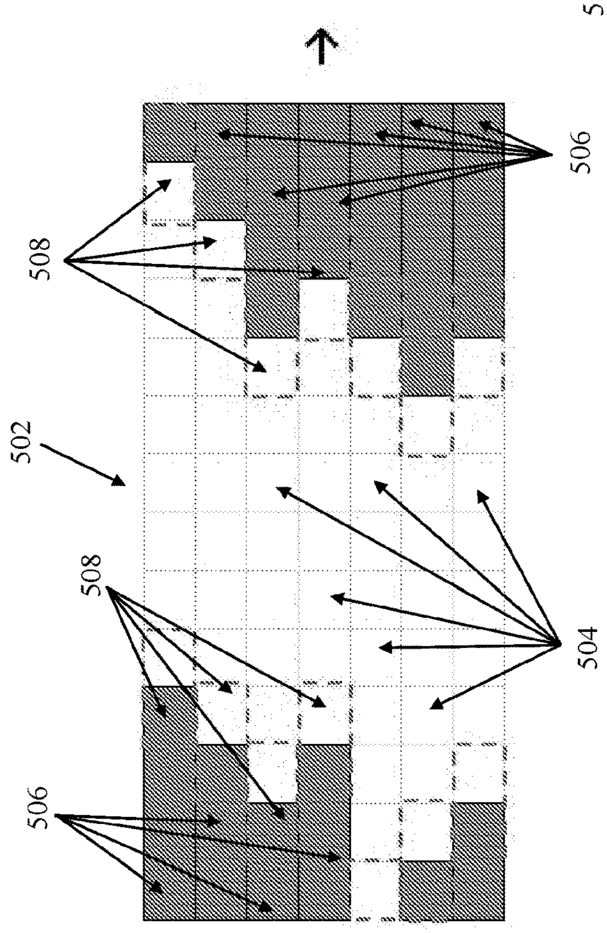

Referring to FIGS. 6A and 6B, diagrams illustrating generation of a trust or search region are shown, according to example embodiments of the current disclosure. FIGS. 6A and 6B show an aperture (or a cross-sectional area of a radiation beam) 502 that is discretized or segmented into a plurality of beamlets (or beamlet cross-sectional areas) 504. For each leaf 506, a corresponding movement range 508, illustrated as a dashed rectangle, is defined in terms of the current position of the leaf 506. For each leaf 506, the corresponding movement range 508 is defined as a spatial region having a first dimension (e.g., width) equal to a dimension (e.g., width) of the leaf 506 and a second dimension extending from a beamlet backward to a beamlet backward, with respect to the current location of the leaf 506.

The computing system 150 can determine the search or trust region as the combination of the movement ranges for various leaves. The beamlets 504 can be classified into three categories. For instance, referring to FIG. 6B, a first category 510 represents closed or fully covered beamlets in the current solution that would stay closed in the next solution. A second category 512 represents open beamlets in the current solution that would stay open in the next solution. A third category represents beamlets whose states in the next iteration are unknown and depend on the motion of the corresponding leaves. Each of these categories can be viewed as a spatial region including beamlets of that category leading to three spatial regions 510, 512 and 514 forming the aperture 502. The third category 514 can be viewed as representing the search or trust region. The search or trust region 514 can be defined as including the movement ranges 508 for the plurality of leaves 506, or as the spatial region where variation in beamlets' states is possible when moving from the current solution to the next solution of the non-convex VMAT optimization problem. The search or trust region 514, in the illustrative example of FIG. 6B, includes three disjoint spatial regions, each of which defined as a combination of a corresponding subset of the movement ranges 508. The first beamlet category 510 can be viewed as representing a region 510 of fully closed or covered beamlets in the current and next solution. The first beamlet category 512 can be viewed as representing a region 512 of fully open or exposed beamlets in the current and next solution.

Referring now to FIGS. 1A, 1B, 5, 6A and 6B, the method 400 can include the computing system 150 merging, for each spatial movement range associated with a corresponding leaf of the plurality of leaves, beamlets associated with the spatial movement range (STEP 404). For each movement range 508 of a corresponding leaf 506, the computing system 150 can merge the beamlets 504 overlapping with, or forming, the movement range 508 into a single beamlet. In the illustrative example of FIG. 6A, each movement range 508 of a corresponding leaf 506 includes (or overlaps with) two corresponding beamlets 504 where one beamlet 504 is currently covered by the leaf 506 and one beamlet 504 is currently exposed. The computing system 150 can merge the beamlets 504 forming, or overlapping with, a corresponding movement range 508 of a corresponding leaf 506 into a single beamlet that is larger in size than the original beamlets 504. As such, the search or trust region 514 includes a single beamlet per aperture row after the merging.

The method 400 can include the computing system 150 transforming, based on the merging of the beamlets, the non-convex VMAT optimization problem into a convex VMAT optimization problem or approximation (STEP 406). By merging the beamlets (e.g., two beamlet in FIG. 6A) associated with each spatial moving range 508 of a corresponding leaf 506 into one beamlet, the computing system 150 can reduce or transform the original non-convex VMAT optimization problem, e.g., described by equations (1)-(7), into a convex approximation problem. As mentioned earlier, the main source of the non-convexity is the constraint in (4) ($x=\Phi(\eta, l, r)$) and/or the formulation of the function $\Phi(\eta, l, r)$, for example, as described in equation (7). For the regions 510 and 512 (or first and second beamlet categories), the function $\Phi$ is equal to zero and $\eta$ respectively. However, within the search or trust region 514, the function $\Phi$ is between zero and $\eta$ depending on how the current position of the corresponding leaf and how it moves (e.g., backward or forward).

Given that for each beam, all the open beamlets in region 512 have the same intensity $\eta_b$, the computing system 150 can also merge these beamlets into a single beamlet, referred to hereinafter as interior beamlet 512. Accordingly, the computing system 150 can transform or reduce the non-convex VMAT optimization problem into the following convex fluence map optimization problem:

$$\min_{X} \hat{F}(\hat{x}) = \sum_{s\in\{PTV\}} \left\|\hat{A}^s \hat{x} - p\right\|_2^2 \tag{8}$$

$$\text{subject to: } \begin{cases} \max\left(\hat{A}^s \hat{x}\right) \le d_s^{max}:\ s \in S_{max} & (9) \\ \text{mean}\left(\hat{A}^s \hat{x}\right) \le d_s^{mean}:\ s \in S_{mean} & (10) \\ \hat{x}_b = \eta_b:\ b = 1, \ldots, B & (11) \\ 0 \le \hat{x}_{b,k} \le \eta_b:\ b = 1, \ldots, B;\ k = 1, \ldots, K_b & (12) \\ 0 \le \eta \le U^\eta & (13) \end{cases},$$

where $\hat{x}_b$ and $\hat{x}_{b,k}$ represent the intensity of the interior beamlets 512 and the $k^{th}$ beamlet in the search or trust region 514 for beam b, respectively. The matrix $\hat{A}^s$ can represent the adjusted influence matrix. In the above problem, the computing system 150 can eliminate the variable $\eta$ and the constraint in equation (11), and modify or replace the constraints in equations (12) and (13) with $0\le\hat{x}_{b,k}\le\hat{x}_b$ and $0\le\hat{x}_b\le U^\eta$, respectively. The convex VMAT optimization problem described equation (8)-(11), or by equations (8)-(10) and the modified equations (12) and (13), can represent an equivalent or an approximation of the original non-convex VMAT optimization problem defined by equations (1)-(6) around the current solution. Note that the convex formulation depicted by equations/inequalities (8)-(13) does not include equations corresponding to fully covered beamlets 510 (e.g., beamlets with beamlet intensity equal to zero) as these beamlets have zero contribution to the term $A^s x$.

The method 400 can include the computing system 150 solving the convex VMAT optimization problem to determine new positions of the plurality of leaves (STEP 408). The computing system 150 can solve the convex VMAT optimization problem described equation (8)-(11), or by equations (8)-(10) and the modified equations (12) and (13), using linear programming techniques or other techniques known in the art to determine the vectors $\hat{x}_b$ and $\hat{x}_{b,k}$. After solving this convex problem, computing system 150 can determine or reconstruct the primary variables (η, l, r) using the vectors $\hat{x}_b$ and $\hat{x}_{b,k}$.

Figure 7:
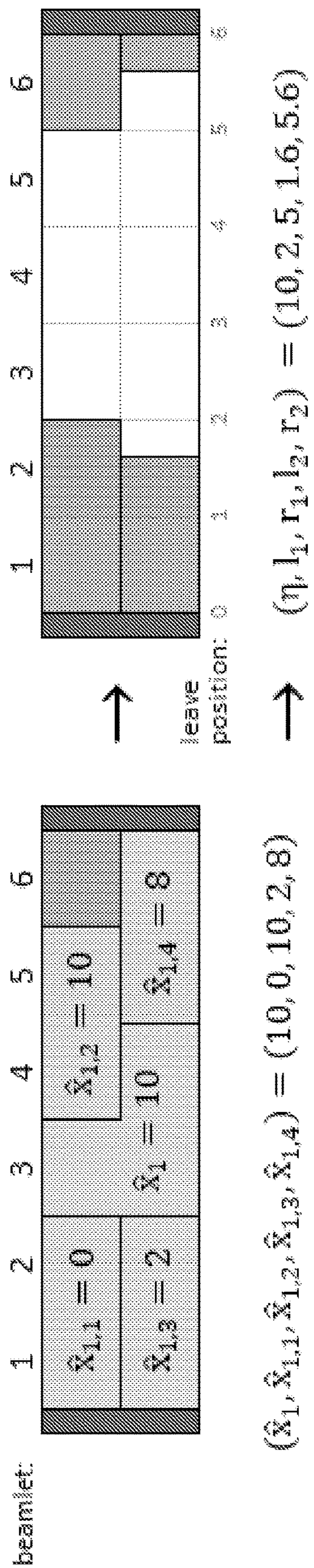
FIG. 7 shows a diagram illustrating reconstruction of primary variables from an optimal solution of a convex approximation of the VMAT optimization problem, according to example embodiments of the current disclosure.

Referring to FIG. 7, a diagram illustrating the reconstruction of the primary variables from an optimal solution of the convex approximation of the VMAT optimization problem is shown, according to some example embodiments of the current disclosure. Starting at the interior beamlet satisfying equation (11), the computing system 150 can use the equation $\hat{x}_1=10$ to determine that $\eta_1=10$. The computing system 150 can use the equation $\hat{x}_{1,1}=0$ to determine that the first two beamlets of the first row are fully covered or closed. Considering the fact that the second and third beamlets of the first row satisfy the equations $\hat{x}_{1,1}=0$ and $\hat{x}_1=10$, respectively, the computing system 150 can deduce that $l_1=2$. Also, given that the fourth and fifth beamlets, which form the movement range of the first right leaf, satisfy the equation $\hat{x}_{1,2}=10\eta_1$, the computing system 150 can determine that $r_1=5$. Using the equation $$\hat{x}_{1,3} = 2 = \frac{\eta_1}{5},$$

which applies to the first and second beamlets of the second row, the computing system 150 can determine that $$l_2 = 2 \times \left(1 - \frac{1}{5}\right) = 1.6.$$

Finally, using the equation $$\hat{x}_{1,4} = 8 = \frac{4}{5}\eta_1,$$

which applies to the fifth and sixth beamlets of the second row, the computing system 150 can determine that $$r_2 = 4 + 2 \times \frac{4}{5} = 5.6.$$

Therefore, the new solution is $(\eta_1, l_1, r_1, l_2, r_2)$=(10, 2,5,1.6, 5.6).

It is worth mentioning that when the search or trust region is defined to allow each leaf to move only one beamlet either forward or backward, e.g., as described in FIGS. 6A and 6B, then the convex problem (e.g., as defined by equations (8)-(13)) derived by merging the beamlets within each leaf movement range or within the search or trust region represents an exact transformation, not an approximation, of the original non-convex problem (e.g., as described by equations (1)-(6)). However, if the search or trust region is defined to be wide enough to allow leaves to move multiple beamlets forward or backward, the corresponding convex problem defined by merging the beamlets within each leaf movement range or within the search or trust region becomes an approximation of the original non-convex problem. In fact, the wider the trust region (e.g., the more beamlets along which a leaf can travel) the less accurate and more global the convex approximation. The number of beamlets that leaves can travel is referred to hereinafter as the step-size.

The steps 402-408 of the method 400 can be repeated iteratively until a satisfactory solution of the non-convex VMAT optimization problem is reached. After solving the convex approximation problem (e.g., at the end of the $k^{th}$ iteration) and obtaining the primary variables (η, l, r), the computing system 150 can compare the obtained primary variables to the previous solution $(\eta^k, l^k, r^k)$ using the actual non-convex problem and objective function F. Specifically, the computing system 150 can evaluate F(x) using (η, l, r) and $(\eta^k, l^k, r^k)$, respectively, and compare both values of F(x). The computing system 150 can check whether the new solution (η, l, r) satisfies the constraints in equations (2)-(6) of the original non-convex problem. The computing system 150 can accept (η, l, r) as the new solution $(\eta^{k+1}, l^{k+1}, r^{k+1})$ of the non-convex problem, if it determines that (η, l, r) is a better solution) of the non-convex VMAT optimization problem than $(\eta^k, l^k, r^k)$. For example, if the computing system 150 determines that (η, l, r) results in a reduction in F(x) compared to $(\eta^k, l^k, r^k)$ and that (η, l, r) satisfies the constraints in equations (2)-(6), the computing system 150 can use (η, l, r) as the current solution $(\eta^{k+1}, l^{k+1}, r^{k+1})$ of the non-convex VMAT optimization problem in the next iteration k+1. Otherwise, the computing system 150 can reject (η, l, r) and may seek a different solution.

When the non-convex VMAT optimization problem is approximated (e.g., a relatively wide search or trust region is used), the solution (η, l, r) of the convex problem may not present an improved solution of the non-convex VMAT optimization problem, or it may even be infeasible and violate constraint (2) or (3). In case of infeasibility, the computing system 150 can determine or compute another solution, for example, by preserving the determined leave positions (l, r) and re-optimizing the aperture intensities η in the original problem. Such re-optimization amounts to a convex fluence map optimization problem. If the solution (η, l, r) is not better than the previous (or current) solution $(\eta^k, l^k, r^k)$, then the computing system 150 can determine or construct a new convex approximation by changing the trust region or the step size. Algorithm 1 below illustrates an example pseudocode implementation of method 400 or the SCP-based approach for solving the non-convex VMAT optimization problem. The algorithm starts with leave positions adjusted according to the beam's eye view (BEV) of the target region, and usually a relatively large search or trust region or a relatively large step size. At each iteration of Algorithm 1, the computing system 150 can generate a new solution by solving the convex approximation problem. If the solution is infeasible, then the computing system 150 can re-optimize the aperture intensities to turn it into a feasible solution. If the determined solution (η, l, r) at the $k^{th}$ iteration is better than the current solution $(\eta^k, l^k, r^k)$ at that iteration, the computing system 150 can update, the current solution to be used in the next iteration k+1 to be $(\eta^{k+1}, l^{k+1}, r^{k+1})$=(η, l, r) and enlarge or increase the search or trust region (or the step size) to promote a global search. Otherwise, the computing system 150 can reject the solution (η, l, r), and shrink or decrease the search or trust region (or the step size) to create a more accurate convex approximation.

Algorithm 1. The pseudocode for the proposed algorithm.

```
Initialize the leave positions (BEV of target) and step-size
while improvement > ε do
  find the auxiliary solution x̂^k by optimizing the convex approximation problem
  reconstruct the actual solution (η, l, r)
    if (η, l, r) is infeasible then
      use (l, r) and reoptimize n to generate a feasible solution (easy convex problem)
    endif
    if (η, l, r) is better than (η^k, l^k, r^k) then
      update the solution (η^{k+1}, l^{k+1}, r^{k+1}) = (η, l, r)
      enlarge the trust region (step-size = step-size + 1)
    else
      shrink the trust region (step-size = round(step-size/2))
    endif
  k ← k + 1
end while
```

D. Simulation Results

Simulation results described herein are compared to a ground truth using convex mixed integer nonlinear programs (MINLP) formulation. While there is no efficient optimization algorithm to solve a general (even small) non-convex optimization problem to global optimality, there are few classes of non-convex problems, including convex MINLP that can be solved to global optimality. A MINLP problem is inherently a non-convex problem due to the presence of discrete variables. However, if the discrete variables are the solely source of the non-convexity and the corresponding relaxed problem defined by replacing the discrete variables with continuous or real-number variables is convex, then the relaxed problem is referred to as convex MINLP for which a small/medium size problem can be solved to global optimality.

To provide a convex MINLP formulation, one can restrict the leaf position variables (l, r) to be only integer numbers, meaning each beamlet could be either fully open or fully closed. An auxiliary binary variable z can be introduced for each beamlet that takes the value zero or one if the beamlet is closed or open, respectively. Referring to the non-convex VMAT optimization problem defined by equations (1)-(6), one can replace constraint (4) with the following set of constraints for each beamlet $i \in I$:

$$r_{b_ir_i} - c_i \times z_i \geq 0 \ (z_i = 0 \text{ if the right leaf covers beamlet } i) \tag{14}$$

$$(N + 1 - c_i) \times z_i + l_{b_ir_i} \leq N \ (z_i = 0 \text{ if the left leaf covers beamlet } i) \tag{15}$$

$$\sum_{i \in I_{br}} z_i = r_{br} - l_{br} \tag{16}$$

$(z_i = 1$ if neither left nor right *leaaves* covers beamlet $i)$ $$0 \leq x_i \leq U^{\eta} \times z_i \ (x_i = 0 \text{ if } z_i = 0) \tag{17}$$

$$\eta_{b_i} - U^{\eta} \times (1 - z_i) \leq x_i \leq \eta_{b_i} (x_i = \eta_{b_i} \text{ if } z_i = 1) \tag{20}$$

$$z_i\text{: binary; } l_{b_ir_i}, r_{b_ir_i}\text{: integer} \tag{21}$$

where beamlet i belongs to beam $b_i$, row $r_i$ and column $c_i$. The variables $l_{b_ir_i}$ and $r_{b_ir_i}$ represent the positions of the left and right leaves, respectively, corresponding to beamlet i. The binary variables are commonly used in mathematical modeling to translate "if conditions" into mathematical formulations. It is worth mentioning that constraint (21) is the only source of non-convexity here, making the problem a convex MINLP.

Referring back to FIG. 7, one can apply the above constraints (14)-(21) to the first row of the solution on the right side of the figure where (η, l, r, N)=(10, 2, 5, 6). For the first and second beamlets ($z_1$ with $c_1=1$, and $z_2$ with $c_2=2$), constraint (15) become $((6+1-1)\times z_1+2\leq 6)$ and $((6+1-2)\times z_2+2\leq 6)$, enforcing $z_1=z_2=0$ given that $z_i$ can only be 0 or 1. For the sixth beamlet, constraint (14) becomes $(5-6\times z_{6\geq 0})$, enforcing $z_6=0$. Constraint (16) can be written as $$\sum_{i=1}^{6} z_i = 3$$

leading to $z_3=z_4=z_5=1$. Given that $z_1=z_2=z_6=0$ and $z_3=z_4=z_5=1$, Constraint (19) enforce $x_1=x_2=x_6=0$ and Constraint (6) enforce $x_3=x_4=x_5=\eta$.

In the simulations discussed below, the proposed SCP-based VMAT algorithm is implemented in MATLAB (The MathWorks, Inc., Natick, MA) on a PC with 2.4 GHz Intel Xeon CPU and 64 GB RAM. At each iteration, the resultant convex optimization problem is solved using Artelys KNITRO™ (Artelys Corp., Chicago, IL). To obtain the ground-truth, the resultant MINLP problem is solved using GUROBI™ (GUROBI Optimization Inc., Beaverton, OR). KNITRO and GUROBI are commerical optimization engines specialized in constrained non-linear programming and mixed integer programming, respectively.

Three previously treated patients with different disease sites (prostate, oligometastasis and paraspinal) are used in this study. The optimization parameters (PTV prescription, OAR max/mean dose constraints $$d_s^{max}/d_s^{mean})$$

are defined based on predefined institution clinical criteria. The dose influence matrix is pre-calculated and stored using Eclipse™ API (application programming interface) for 72 evenly spaced beams (representing a full arc). The beamlet resolution of 10 mm×10 mm is used and Eclipse API point cloud function is employed to descritize each patient's body. Table 2 below summarizes the patients' data.

TABLE 2

Data summary for high-resolution patient cases.

| Tumor type | PTV size (cc) | # of beamlets | # of points | Prescription |
|---|---|---|---|---|
| Prostate | 84.5 | 3607 | 80800 | 5 Gy in 5 fractions |
| Oligometastasis | 4.8 | 657 | 52949 | 24 Gy in 1 fraction |
| Paraspinal | 22.6 | 1571 | 55845 | 24 Gy in 1 fraction |

Figure 8:
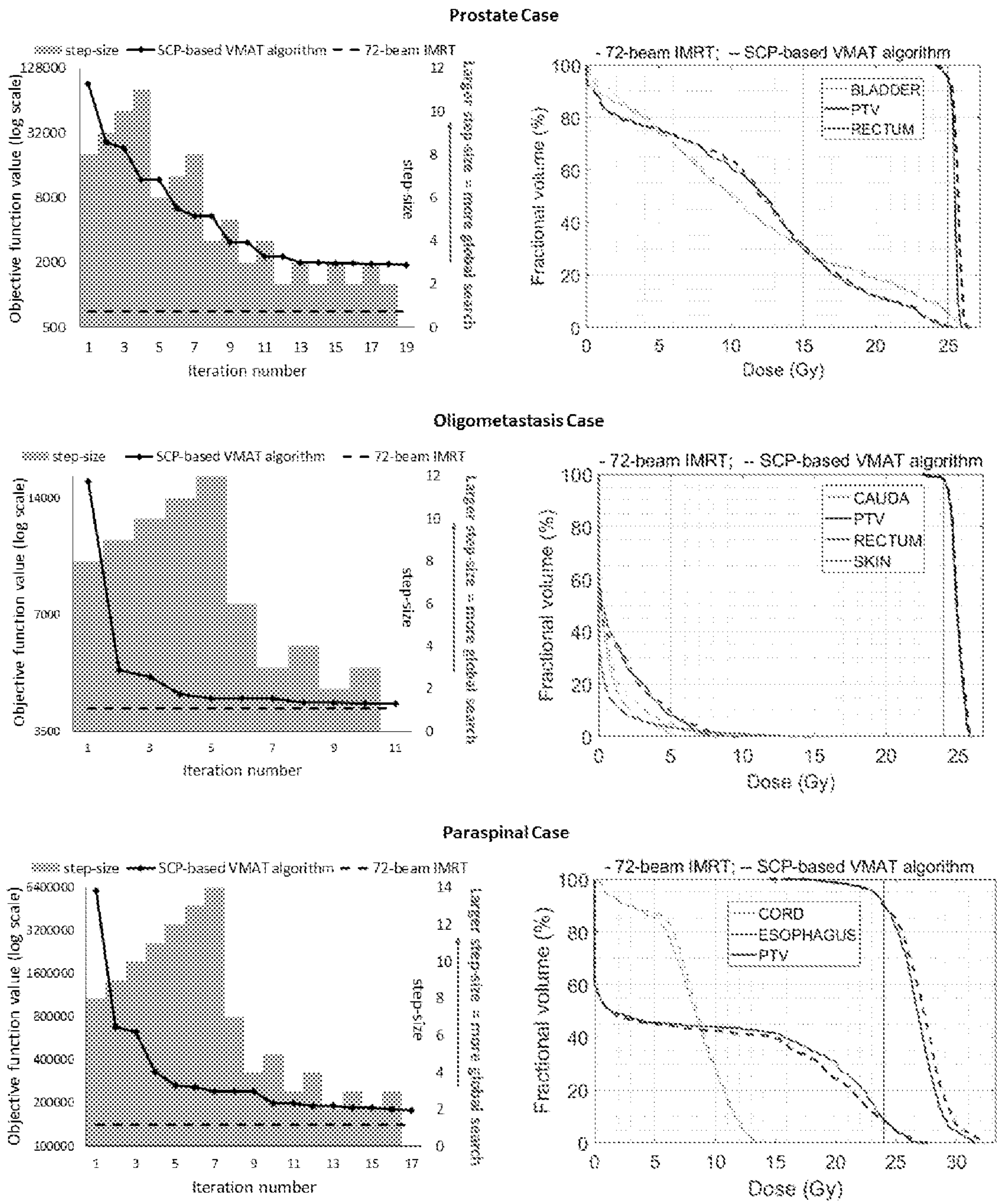
FIG. 8 shows graphs illustrating simulation results for three different patients.

Referring to FIG. 8, graphs illustrating simulation results for three different patients are shown. The simulation results in each row correspond to one of the three patients in Table 1. The graphs on the left side (or left column) of FIG. 8 illustrate the convergence behavior of the algorithm or the change in the objective function F(x) over multiple iterations. The x-axis in the left graphs represents the iteration number and the primary y-axis (left y-axis) represents the objective function value in the logarithmic scale. The solid line, in each graph in the left column, represents the algorithm objective function value F(x) at each iteration and the dashed line represents the IMRT objective function value used as a benchmark. The vertical bars represent the step size used at each iteration with the step size values represented in the secondary y-axis (right y-axis). The step size in all three left graphs is represented in units of to 2.5 mm, whereas the beamlet size is 10 mm. For the prostate case (top left figure), the algorithm starts with the BEV of PTV as the initial point for the left and right leaves and the step size=8 (8*2.5 mm=20 mm). The first four iterations successfully improve the objective function (from 91 000 to 12 000) and therefore the algorithm keeps increasing the step size (from 8 to 11) to further promote the global search. The algorithm fails to make any progress at iteration five, which implies that the convex approximation is inaccurate and its optimal solution does not improve the solution of the original non-convex problem. The algorithm then decreases the step size to 6 (15 mm) to improve the accuracy of the convex approximation by shrinking the trust-region. The more accurate/local convex approximation succeeds in improving the objective function and the algorithm proceeds until iteration 19 when there is a negligible improvement in the objective function. For all three cases, the algorithm takes 11-19 iterations (15.7 on average) and 7-143 mins (72 mins on average) to terminate.

The graphs in the right column of FIG. 8 show the dose volume histogram (DVH) of the VMAT plans generated by the SCP-based algorithm (shown in dashed lines) and the DVH of the ideal (i.e., optimal fluence map plan before leaf sequencing) 72-beam IMRT plans (shown in solid lines). The x-axis in these graphs represents the dose while the y-axis represents the fractional volume. The DVH plots show that the VMAT plans are very similar to the IMRT plans for all three patient cases. For the oligometastasis case, the cauda dose is less for the IMRT plan. However, the cauda dose is way less than the maximum threshold value of 16.66 Gy for both plans. For the paraspinal case, the two plans have a slightly different trade-offs between PTV coverage/homogeneity and OAR sparing, with VMAT plan being superior in OAR sparing and IMRT plan being superior in PTV coverage/homogeneity.

Figure 9:
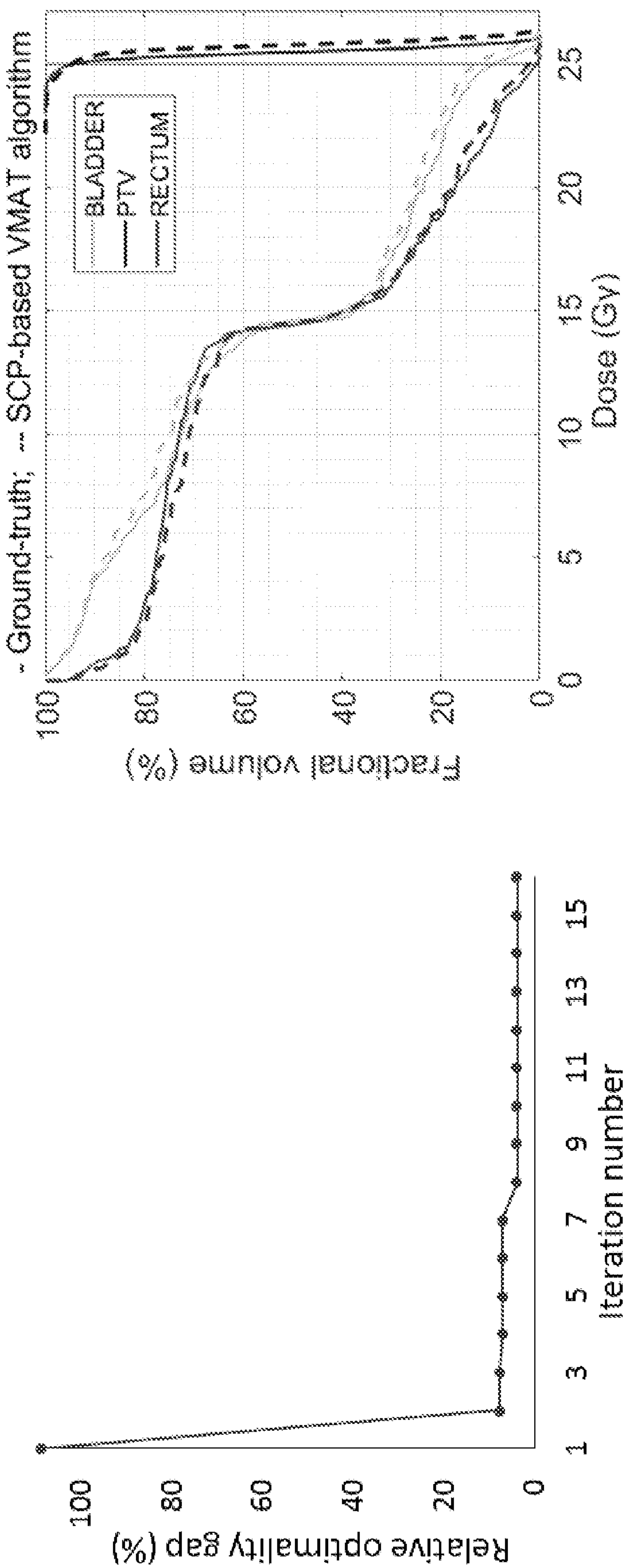
FIG. 9 shows graphs illustrating a comparison between simulation results for the ground-truth plan and the plan generated by the SCP-based approach.

Referring to FIG. 9, graphs illustrating a comparison between simulation results for the ground-truth plan and the plan generated by the SCP-based approach are shown. The ground-truth plan is generated using a MINLP formulation. While in principle a convex MINLP problem can be solved to global optimality, the size of the problem that can be solved is limited based on the available computational platform (i.e., hardware and software) and the time constraint. The ground-truth VMAT plan for the down-sampled prostate case (only x beams) is obtained by solving the convex MINLP problem using GUROBI. The down sampling is only performed on the beam selection process and a full resolution data is used otherwise (e.g., number of points, beamlet resolution). Given that the MINLP formulation assumes that the leave positions are integer values (i.e., leave cannot park in the middle of the beamlets), the same restrictive assumption is also made in the SCP-based algorithm to have a fair comparison to validate the proposed algorithm. It is to be noted that such restrictive assumption hinders the performance or accuracy of the SCP-based algorithm, which is capable of handling continuous variables.

The dose-volume histogram (DVH) of the ground-truth plan is shown in solid lines in the right graph of FIG. 9, and the DVH of plan generated by the SCP-based algorithm is shown dashed lines. The plans are similar, with ground-truth being slightly better in terms of PTV coverage/homogeneity and OAR sparing. However, the computational complexities, or processing times, are quite different. While the SCP-based algorithm converges in minutes, the ground-truth approach converges in hours. In terms of the objective function value and as illustrated in the left graph of FIG. 9, the SCP-based algorithm provides a solution with 3.8% relative optimality gap (compared to the ground-truth approach). It means the algorithm can efficiently generate a high-quality solution in the proximity of the global optimal solution.

The embodiments described herein presents a new approach based on the sequential convex programming technique to optimize the machine parameters directly for VMAT. The non-convexity challenge of the VMAT optimization problem can be tackled by iteratively solving a series of convex optimization problems approximating the original problem locally and globally. The convex approximations can be derived at each iteration by constraining the leaf motions and merging some neighboring beamlets. In the SCP-based approach, approximating the original non-convex VMAT optimization problem over a larger search or trust region leads to a global approximation (not an exact representation that promotes, but does not necessarily guarantee, global convergence of the algorithm. Local approximations (with relatively smaller search or trust regions), on the other hand, provide further refinements and ensure the local optimality of the solution. Given that for a small local search space, e.g., each leaf only moves within a beamlet backward or forward, the convex problem is an exact representation of the original non-convex problem, the local optimality is guaranteed (not necessarily global optimality). In fact, when it comes to a large-scale non-convex optimization problem, usually convergence to a good local optimal solution in a reasonable amount of time is desirable and expected. The simulation results discussed above confirm that the SCP-based approach converges to a good local optimal solution for a down-sampled problem by comparison with a global optimal solution provided by solving the computationally expensive MINLP problem.

The simulation results for the three patients with small/medium PTV sizes show that the SCP-based approach can converge in 11-19 iterations and 7-143 minutes. In some implementations, the computational performance can be improved by using a better initial solution, for example, using a two-step technique or column generation, as opposed to using the BEV of the PTV as the initial aperture shapes. In general, constrained optimization is computationally much more expensive than unconstrained optimization. However, constrained optimization is a very powerful tool for automated treatment planning and saves a lot of time that otherwise would be spent on parameter tuning. Using constrained optimization, the PTV and OAR max/mean constraints can be met by expressing them as hard constraints and without any parameter tweaking. In some implementations, an automated VMAT planning can be developed using a hierarchical constrained optimization framework. For example, after solving the optimization problem using the SCP-based approach as a first step, one can solve an extra optimization problem (second step) to further lower the OAR doses beyond the required max/mean dose hard constraints while preserving the results of the first step.

The treatment plan delivery efficiency and machine constraints are not incorporated in the problem formulations discussed above. In some implementations, specific machine constraints, such as MLC speed limits or MU limits, can be added as hard constraints. In some implementations, one or more regularization terms can be added in the objective function F(x) to promote the plan delivery efficiency. For example, the regularization term(s) can penalize discrepancies between neighboring apertures (or neighboring leaves).

According to example embodiments, automated VMAT-based treatment palaning can be achieved using a new approach based on sequencial convex programming. While direct machine parameter optimization for VMAT is inherently a challenging non-convex optimization problem, the proposed approach is shown to generate high-quality VMAT plans close to the ideal IMIRT plans. The proximity of the solution to the global optimal solution is confirmed on a down-sampled case by comparison to the ground-truth solution obtained via a computationally expensive MINLP approach.

Each method described in this disclosure can be carried out by computer code instructions stored on computer-readable medium. The computer code instructions, when executed by one or more processors of a computing device, can cause the computing device to perform that method.

While the disclosure has been particularly shown and described with reference to specific embodiments, it should be understood by those skilled in the art that various changes in form and detail may be made therein without departing from the spirit and scope of the invention described in this disclosure.

While this disclosure contains many specific embodiment details, these should not be construed as limitations on the scope of any inventions or of what may be claimed, but rather as descriptions of features specific to particular embodiments of particular inventions. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

What is claimed is:

1. A method of volumetric modulated arc therapy (VMAT) treatment planning, comprising:

(a) determining, by one or more processors, using a current solution of a non-convex VMAT optimization problem, a search region defining, for each leaf of a plurality of leaves of a multi-leaf collimator (MLC), a corresponding spatial movement range, the current solution including a first set of positions for the plurality of leaves of the MLC;

(b) merging, by the one or more processors, for each spatial movement range of a corresponding leaf, beamlets associated with the spatial movement range;

(c) transforming, by the one or more processors, the non-convex VMAT optimization problem into a convex VMAT optimization based on the merging of beamlets associated with each spatial movement range;

(d) solving, by the one or more processors, the convex VMAT optimization problem to determine a second set of positions for the plurality of leaves of the MLC;

(e) comparing, by the one or more processors, a performance of the second set of positions for the plurality of leaves of the MLC and a performance of the current solution with respect to solving the non-convex VMAT optimization problem; and (f) modifying, by the one or more processors, for each leaf of the plurality of leaves of the MLC, the corresponding spatial movement range, based on comparing the performance of the second set of positions for the plurality of leaves of the MLC and the performance of the current solution.

2. The method of claim 1, wherein the current solution includes one or more first aperture intensity values and solving the convex VMAT optimization problem includes determining one or more second aperture intensity values.

3. The method of claim 1, wherein the non-convex VMAT optimization problem is formulated using an objective function and a plurality of hard constraints.

4. The method of claim 3, wherein the plurality of hard constraints include a constraint limiting an average radiation dose or a maximum radiation dose within an organ at risk (OAR).

5. The method of claim 3, wherein the objective function includes a regularization term penalizing discrepancies between neighboring apertures.

6. The method of claim 1, further comprising:
repeating, by the one or more processors, steps (a)-(d) for a plurality of iterations including comparing, at each iteration, the performance of the second set of positions for the plurality of leaves of the MLC to the performance of the current solution with respect to solving the non-convex VMAT optimization problem.

7. The method of claim 6, further comprising:
replacing the current solution with the second set of positions for the plurality of leaves of the MLC, upon determining that the performance of the second set of positions for the plurality of leaves of the MLC is better than the performance of the current solution.

8. The method of claim 6, wherein modifying the corresponding spatial movement range further comprises:
increasing, for each leaf of the plurality of leaves of the MLC, the corresponding spatial movement range, upon determining that the performance of the second set of positions for the plurality of leaves of the MLC is better than the performance of the current solution; or
decreasing, for each leaf of the plurality of leaves of the MLC, the corresponding spatial movement range, upon determining that the performance of the second set of positions for the plurality of leaves of the MLC is worse than the performance of the current solution.

9. The method of claim 6, wherein the current solution includes one or more first aperture intensity values and the solving the convex VMAT optimization problem includes determining one or more second aperture intensity values, and the method further comprising:
using the second positions of the plurality of leaves of the MLC to compute one or more third aperture intensities, upon determining that the second set of positions for the plurality of leaves of the MLC and the one or more second aperture intensities violate a constraint of a plurality of hard constraints of the non-convex VMAT optimization problem.

10. The method of claim 1, wherein the non-convex VMAT optimization problem is defined using patient specific data.

11. A system for performing volumetric modulated arc therapy (VMAT) treatment planning, the system comprising:
one or more processors; and
a memory to store computer code instructions, the computer code instructions when executed cause the one or more processors to:
determine, using a current solution of a non-convex VMAT optimization problem, a search region defining, for each leaf of a plurality of leaves of a multi-leaf collimator (MLC), a corresponding spatial movement range, the current solution including a first set of positions for the plurality of leaves of the MLC;
merge, for each spatial movement range of a corresponding leaf, beamlets associated with the spatial movement range;
transform the non-convex VMAT optimization problem into a convex VMAT optimization based on the merging of beamlets associated with each spatial movement range;
solve the convex VMAT optimization problem to determine a second set of positions for the plurality of leaves of the MLC;
compare a performance of the second set of positions for the plurality of leaves of the MLC and a performance of the current solution with respect to solving the non-convex VMAT optimization problem; and
modify, for each leaf of the plurality of leaves of the MLC, the corresponding spatial movement range, based on comparing the performance of the second set of positions for the plurality of leaves of the MLC and the performance of the current solution.

12. The system of claim 11, wherein the current solution includes one or more first aperture intensity values and solving the convex VMAT optimization problem includes determining one or more second aperture intensity values.

13. The system of claim 11, wherein the non-convex VMAT optimization problem is formulated using an objective function and a plurality of hard constraints.

14. The system of claim 11, wherein the computer code instructions when executed cause the one or more processors to repeat steps (a)-(d) for a plurality of iterations including comparing, at each iteration, the performance of the second set of positions for the plurality of leaves of the MLC to the performance of the current solution with respect to solving the non-convex VMAT optimization problem.

15. The system of claim 14, the computer code instructions when executed cause the one or more processors to modify the corresponding spatial movement range by:
increasing, for each leaf of the plurality of leaves of the MLC, the corresponding spatial movement range, upon determining that the performance of the second set of positions for the plurality of leaves of the MLC is better than the performance of the current solution; or
decreasing, for each leaf of the plurality of leaves of the MLC, the corresponding spatial movement range, upon determining that the performance of the second set of positions for the plurality of leaves of the MLC is worse than the performance of the current solution.

16. A computer readable non-transitory medium including computer code instructions stored thereon, the computer code instructions when executed cause one or more processors to:
determine, using a current solution of a non-convex VMAT optimization problem, a search region defining, for each leaf of a plurality of leaves of a multi-leaf collimator (MLC), a corresponding spatial movement range, the current solution including a first set of positions for the plurality of leaves of the MLC;
merge, for each spatial movement range of a corresponding leaf, beamlets associated with the spatial movement range;
transform the non-convex VMAT optimization problem into a convex VMAT optimization based on the merging of beamlets associated with each spatial movement range;
solve the convex VMAT optimization problem to determine a second set of positions for the plurality of leaves of the MLC;
compare a performance of the second set of positions for the plurality of leaves of the MLC and a performance of the current solution with respect to solving the non-convex VMAT optimization problem; and
modify, for each leaf of the plurality of leaves of the MLC, the corresponding spatial movement range, based on comparing the performance of the second set of positions for the plurality of leaves of the MLC and the performance of the current solution.

17. The computer readable non-transitory medium of claim 16, wherein the current solution includes one or more first aperture intensity values and solving the convex VMAT optimization problem includes determining one or more second aperture intensity values.

18. The computer readable non-transitory medium of claim 16, wherein the current solution includes one or more first aperture intensity values and solving the convex VMAT optimization problem includes determining one or more second aperture intensity values.

19. The computer readable non-transitory medium of claim 16, wherein the computer code instructions when executed further cause one or more processors to repeat steps (a)-(d) for a plurality of iterations including comparing, at each iteration, the performance of the second set of positions for the plurality of leaves of the MLC to the performance of the current solution with respect to solving the non-convex VMAT optimization problem.

20. The computer readable non-transitory medium of claim 16, wherein the computer code instructions when executed further cause one or more processors to modify the corresponding spatial movement range by:

increasing, for each leaf of the plurality of leaves of the MLC, the corresponding spatial movement range, upon determining that the performance of the second set of positions for the plurality of leaves of the MLC is better than the performance of the current solution; or decreasing, for each leaf of the plurality of leaves of the MLC, the corresponding spatial movement range, upon determining that the performance of the second set of positions for the plurality of leaves of the MLC is worse than the performance of the current solution.

* * * * *